United States Patent [19]

Williamson

[11] Patent Number: 5,460,927
[45] Date of Patent: Oct. 24, 1995

[54] ACTIVATED PROPENES AS COLOR COUPLERS AND A METHOD FOR PRODUCTION OF PHOTOGRAPHIC ELEMENTS THEREWITH

[75] Inventor: Hugh M. Williamson, Hanwell, United Kingdom

[73] Assignee: Eastman Kodak Company, Rochester, N.Y.

[21] Appl. No.: 175,395

[22] PCT Filed: Jun. 29, 1992

[86] PCT No.: PCT/EP92/01476

§ 371 Date: Jan. 3, 1994

§ 102(e) Date: Jan. 3, 1994

[87] PCT Pub. No.: WO93/01523

PCT Pub. Date: Jan. 21, 1993

[30] Foreign Application Priority Data

Jul. 3, 1991 [GB] United Kingdom ............... 9114369

[51] Int. Cl.⁶ ............................................ G03C 7/32
[52] U.S. Cl. ................. 430/449; 430/385; 430/386; 430/543; 558/44; 558/395
[58] Field of Search ............... 558/44, 56, 395; 430/543, 385, 386, 449

[56] References Cited

U.S. PATENT DOCUMENTS

| | | | |
|---|---|---|---|
| 2,459,420 | 1/1949 | Erickson | 558/395 |
| 2,719,861 | 10/1955 | Carboni | 558/360 |
| 3,079,366 | 2/1963 | Boyle et al. | 558/395 |
| 3,398,152 | 8/1968 | Wallace et al. | 558/395 |
| 4,104,049 | 8/1978 | Maurer et al. | 558/395 |

FOREIGN PATENT DOCUMENTS

| | | | |
|---|---|---|---|
| 0431374 | 6/1991 | European Pat. Off. | |
| 0034549 | 11/1975 | Japan | 558/395 |
| 92/14189 | 8/1992 | WIPO | |

*Primary Examiner*—Lee C. Wright
*Attorney, Agent, or Firm*—Arthur E. Kluegel

[57] ABSTRACT

The invention provides a novel and economic method for the production of an activated propene from a malonitrile dimer which comprises reacting a compound of the formula (I)

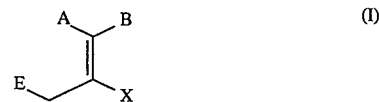

with a nucleophile D to provide a compound of the formula (II)

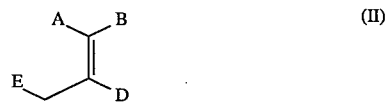

wherein substituents A, B and E each individually represent hydrogen, a substituted or unsubstituted alkyl acyl carboxyl or aryl group or an electron withdrawing group, and X is a group capable of displacement via a substitution reaction.

10 Claims, No Drawings

ACTIVATED PROPENES AS COLOR COUPLERS AND A METHOD FOR PRODUCTION OF PHOTOGRAPHIC ELEMENTS THEREWITH

DESCRIPTION

The present invention relates to activated propenes as color couplers and to a method for their production. The invention particularly relates to magenta color couplers for use in silver halide imaging systems where dyes are formed by oxidative coupling within a photographic layer. Previously pyrazolone couplers such as that described in U.S. Pat. No. -A-2,600,788 have been used. However such pyrazolones are so reactive that the efficiency of dye formation is reduced due to side reactions during photographic processing. Further they require difficult methods of synthesis and have the additional problem of a substantial secondary adsorption peak in the visible spectrum which has an adverse effect on color reproduction.

This problem has been addressed in U.S. Pat. No. -A-4,871,652 by the production of complex cynano-substituted couplers which overcome some of these disadvantages.

A further problem is to produce the activated propenes economically from readily available compounds and with a short reaction sequence.

Our copending British Patent Application No. WO-A-9209010 relates in a first aspect to a photographic composition comprising as a ballasted coupler a propene isomer of the formula

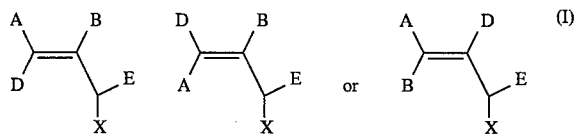

wherein A B and E, each individually represent hydrogen or an electron withdrawing group;

D represents a substituent incorporating a lone pair of electrons, and X is hydrogen or a group releasable during a photographic coupling reaction.

The electron withdrawing group may be selected from selected from hydrogen, —CN, —NO$_2$, —SO$_2$R, —SO$_2$NH—, —CO$_2$R, —COR, —CONHR, —CF$_3$ halogen, amino aryl, aralkyl, alkyl, cycloalkyl, alkyl (carbonyl)oxy, aryl (carbonyl)oxy, carboxy, alkoxycarbonyl, aryloxycarbonyl, carbamomyl, acyl, alkylaminocarbonyl, arylaminocarbonyl, alkoxycarbonylamino, acylamino, ureido, alkylsulphonylamino, arylsulphonylamino, sulphamoylamino, alkylsulphonyl, arylsulphonyl, sulphamoyl, imido, alkylthio, arylthio or a heterocycle;

Examples of the substituent D incorporating the lone pair of electrons are —NH$_2$, —NHR, —NR$^1$R$^2$, —OR, —SR, alkyl (carbonyl) oxy, aryl (carbonyl)oxy, carbamoyl, alkoxycarbonylamino, acylamino, ureido, alkylsulphonylamino, or an arylsulphonylamino group.

In a further aspect of the copending application there is provided a propene isomer of the formula

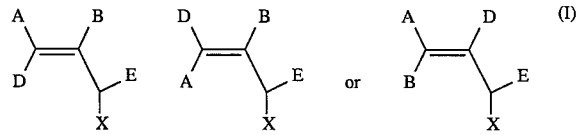

wherein the substituents A, B, E and X are as above defined but wherein D is a group of the formula Ar-L-wherein Ar is a phenyl group optionally substituted with one or more substituents and -L- is a linking group incorporating a lone pair of electrons.

Examples of substituents on Ar are: halogens, —CN, —NO$_2$, —SR, —SO$_2$R, —SO$_2$NHR, —OR, —OCOR, —CO$_2$R, —COR, —CONHR, —CO$_2$H, —NHR, —NR$^1$R$^2$, —NHSO$_2$R, —NHCO$_2$R, —NHCONHR, —CF$_3$, aryl, aralkyl, alkyl and cycloalkyl.

Examples of -L- are: —NH—, —NR—, —N(COR)—, —NHCONH—, —S—, —SO—, —SO$_2$—, —SO$_2$O—, —O— and —(CO)O)O—.

The groups hereinbefore designated R, R$^1$ and R$^2$ are each defined as alkyl or aryl, any of which may be substituted.

U.S. Pat. No. -A-3,079,366 reveals a method for the production of propenes for use as ultraviolet absorbing compounds with plastics materials;

U.S. Pat. No. -A-2,719,861 relates to the manufacture of malononitrile dimer, while EP-A-0,431,374 relates to color couplers and elements containing them.

According to the present invention therefore there is provided a method for the production of a photographic element comprising an activated propene as a color coupler which method comprises reacting a compound of the formula (I)

with a nucleophile D to provide a compound of the formula (II)

wherein A, B and E each individually represent hydrogen, a substituted or unsubstituted alkyl, acyl, carboxy or aryl group or an electron withdrawing group and X is a group capable of displacement via a substitution reaction, and incorporating the same into a photographic element.

The method of the invention may be represented schematically as follows:

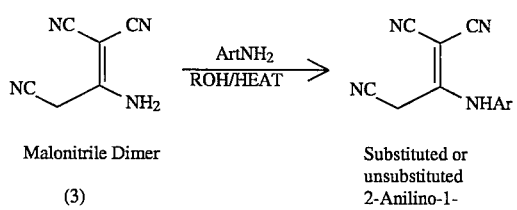

Malonitrile Dimer
(3)

Substituted or unsubstituted 2-Anilino-1-propene 1,1,3-tricarbonitrile

Specific compounds formed in accord with the method of the present invention include:

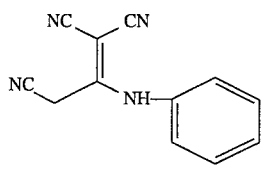

2-Anilino-1-propene-1,1,3-tricarbonitrile       (4)

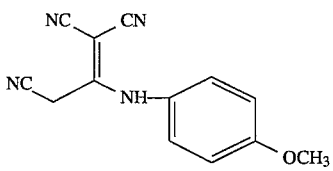

2-(4-methoxyanilino)-1-propene-1,1,3-tricarbonitrile       (5)

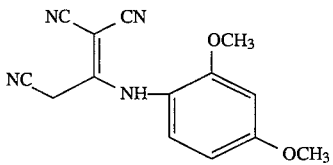

2-(2,4-dimethoxyanilino)-1-propene-1,1,3-tricarbonitrile       (6)

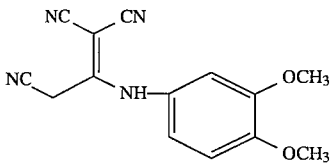

2-(3,4-dimethoxyanilino)-1-propene-1,1,3-tricarbonitrile       (7)

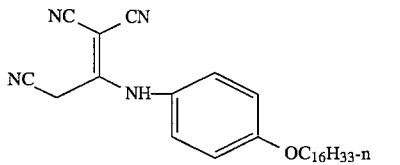

2-(4-Hexadecyloxyanilino-1-propene-1,1,3-tricarbonitrile       (8)

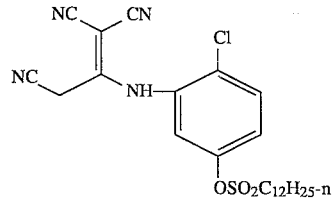

4-Chloro-3-(1,1,3-tricyano-prop-1-en-2-ylamino) phenyl dodecylsulphonate.       (9)

In a preferred form of the invention therefore the substituents A, B and E may be alkyl or substituted alkyl, or may be selected from aralkyl cycloalkyl, alkyl (carbonyl)oxy, alkoxycarbonyl, alkylaminocarbonyl, alkoxycarbonylamino, alkylsulphonylamino, alkylsulphonyl or an alkylthio group.

Alternatively the substituents A, B or E may each individually represent a member selected from a substituted or unsubstituted acyl or aryl group selected from aryl (carbonyl)oxy, arylaminocarbonyl, acylamino, arylsulphonylamino, arylsulphonyl, or arylthio.

In a further embodiment the substituents A, B or E may individually represent a member selected from an unsubstituted carboxy group or an electron withdrawing group selected from —CN, —NO$_2$, —SO$_2$R, —SO$_2$NH—, —COH, —COR, —CONHR, —CF$_3$, carbamoyl, ureido, sulphamoylamino, sulphamoyl, imido, or a heterocycle; wherein R may be a substituted or unsubstituted alkyl or aryl group.

X may be selected from halogen, —NO$_2$, —NH$_2$, —SR, —SO$_2$R, —OSO$_2$R, —OR or OCOR wherein R is defined above.

The activated propenes of the present invention may be incorporated or may be associated, with development inhibitors which are chemical species which are released in an imagewise manner during coupling of the compounds of formula (I) with oxidised color developer under standard processing conditions utilized in color photography. After release, such species interact with the silver halide grain to slow down the development process. This has the effect of increasing the perceived sharpness of the image. Development inhibitors are, for example, sulphur-containing compounds, such as mercaptotetrazoles or mercaptobenzothiazoles, or heterocyclic compounds, such as benzotriazoles or benzothiazoles.

Similarly the active propenes produced by the method of the present invention may incorporate or may be associated with bleach accelerators are chemical species which are released in an imagewise manner during the coupling of compounds of formula (I) with the oxidised color developer in standard conditions. Upon release, such species act to accelerate the rate at which developed silver is bleached from the emulsion layer. This improves the efficiency of the bleaching stage of the development process and so improves the image quality. It also has the potential to reduce the overall processing time. Bleach accelerators, are, for example, sulphur-containing compounds such as soluble alkyl thiols (e.g. mercaptopropionic acid and dimethylaminoethanethiol) or soluble heterocylic thiols.

The aryloxy and thioaryl switch groups act to link a color development inhibitor fragment to a coupler such as a compound of formula (I). Such switches are capable of undergoing an intramolecular rearrangement so as to release the inhibitor fragment. The purpose of the switch group is to delay the release of the inhibitor so the combined switch-inhibitor moiety can diffuse away from the site of initial coupling. By these means, a development inhibitor may be released in a photographic layer adjacent to the site of initial coupling. The release of a development inhibitor in this way results in an improved quality and sharpness.

The above activated propenes react with oxidised color developing agents under alkaline conditions, for example, between pH 10 and 12 to give magenta dyes. The dyes from this process have no significant absorption in the blue region of the visible spectrum and exhibit good coupling activity as compared with conventional couplers.

The couplers made in accordance with the present invention can be incorporated in a photographic element in known manner, for example by incorporation in droplets of coupler solvents.

The photographic element can be a single color element or a multicolor element. In a multicolor element, the magenta dye-forming coupler combinations of this invention would usually be associated with a green-sensitive emulsion, although they could be associated with an emulsion sensitised to a different region of the spectrum, or with a panchromatically sensitised, orthochromatically sensitised or unsensitised emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively. According to the present invention at least one of these magenta dye-forming couplers may be in combination with a substituted phenol. The element can contain additional layers, such as filter and barrier layers.

In the following discussion of suitable materials for use in the emulsions and elements of this invention, reference will be made to Research Disclosure, December 1989, Item 308119, published by Industrial Opportunities Ltd., The Old Harbourmaster's, 8 North Street, Emsworth, Hants PO1O 7DD, U.K. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the propene coupler combinations of this invention, the elements of the invention can include additional couplers as described in Research Disclosure Section VII, paragraphs D, E, F and G and the publications cited therein. The coupler combinations of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilisers (see Research Disclosure Section VI), antistain agents and image dye stabiliser (see Research Disclosure Section VII, paragraphs I and J), light absorbing and scattering materials (see Research Disclosure Section VIII), hardners (see Research Disclosure Section X), plasticisers and lubricants (see Research Disclosure Section XII), antistatic agents (see Research Disclosure Section XIII), matting agents (see Research Disclosure Section XVI), and development modifiers (see Research Disclosure Section The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidise the color developing agent. Oxidised color developing agent in turn reacts with the coupler to yield a dye.

Preferred color developing agents are p-phenylene diamines. Especially preferred are 4-amino-3-methyl-N, N-diethylaniline hydrochloride, 4-amino-3-methyl-N-ethyl-N-β- (methanesulphonamido)-ethylaniline sulphate hydrate, 4-amino-3-methyl-N-ethyl-N-β-hydroethylaniline sulphate, 4-amino-3-β-(methanesulphonamido) ethyl-N, N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The invention will now be described by way of illustration only with reference to the following specific Examples of the invention.

EXAMPLE 1

Preparation of Compound 5

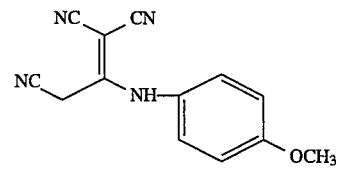

2-(4-Methoxyanilino)- 1,propene-1,1,3 -tricarbonitrile

A solution of p-anisidine (7.38 g; 60 mmol) and 2-amino-1-propene-1,1,3-tricarbonitrile (3.96 g; 30 mmol) in ethanol (75 cm³) was heated under reflux for 72 hours. On cooling, the solution was diluted with ethyl acetate (250 cm³) then washed with dilute hydrochloric acid (2×100 cm³) and brine (100 cm³). The organic layer was separated, dried with magnesium sulphate, filtered then concentrated under reduced pressure to leave a dark colored oil (3.96 g). Pure product was obtained as a buff colored solid (2.2 g; 31%) by column chromatography using silica gel (63–200 mesh) as solid support and ethyl acetate:

60°–80° petroleum in the ratio of 1:1 as eluent. The product exhibited satisfactory mass and NMR spectra.

| $C_{13}H_{10}N_4O$ | C | H | N |
|---|---|---|---|
| Requires:- | 65.5 | 4.2 | 23.5 |
| Found:- | 65.4 | 4.2 | 24.0 |

The following compounds, all of which exhibited satisfactory mass and NMR spectra, were prepared similarly, with the exception that in Example 5 the solvent of choice was THF rather than ethanol.

EXAMPLE 2

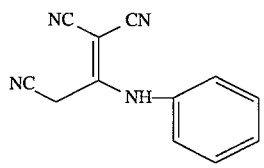

2-Anilino-1-propene-1,1,3-tricarbonitrile

Yield=3%

| $C_{12}H_8N_4$ | C | H | N |
|---|---|---|---|
| Requires:- | 69.2 | 3.85 | 26.9 |
| Found:- | 69.4 | 4.2 | 26.7 |

EXAMPLE 3

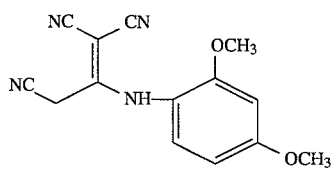

2-(2,4-Dimethoxyanilino)-1-propene-1,1,3-tricarbonitrile

Yield=28%

| $C_{14}H_{12}N_4O_2$ | C | H | N |
|---|---|---|---|
| Requires:- | 62.7 | 4.5 | 20.9 |
| Found:- | 63.3 | 4.4 | 20.7 |

EXAMPLE 4

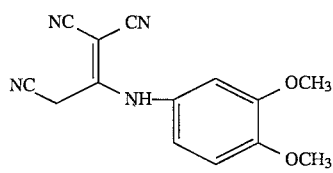

2-(3,4-Dimethoxyanilino)-1-propene-1,1,3-tricarbonitrile

Yield=19%

| $C_{14}H_{12}N_4O_2$ | C | H | N |
|---|---|---|---|
| Requires:- | 62.7 | 4.5 | 20.9 |
| Found:- | 62.9 | 4.6 | 20.5 |

EXAMPLE 5

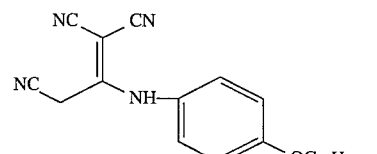

2-(4-Hexadecyloxyanilino)-1-propene-1,1,3-tricarbonitrile

Yield=10%

| $C_{28}H_{40}N_4O$ | C | H | N |
|---|---|---|---|
| Requires:- | 75.0 | 8.9 | 12.5 |
| Found:- | 75.8 | 8.7 | 12.8 |

EXAMPLE 6

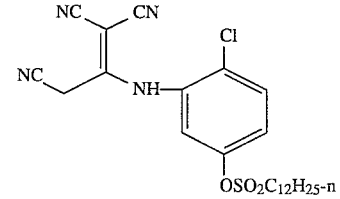

Compound 9:
4-Chloro-3-(1.1.3-tricyano:prop-1-en-2-ylamino)phenyl dodecylsulphonate,

| $C_{24}H_{31}ClN_4O_3S$ | C | H | N |
|---|---|---|---|
| Requires:- | 58.7 | 6.3 | 11.4 |
| Found:- | 58.3 | 6.3 | 11.2 |

EXAMPLE 7

A coupler of formula (9) was incorporated into a photographic, green sensitive silver bromoiodide emulsion and coated in the following format:

| Gel supercoat | gelatin | 1.5 gm |
|---|---|---|
| Emulsion layer | Silver bromoiodide | 1.61 gm$^{-2}$ |
| | Coupler | 1.04 mmolm$^{-2}$ |
| | Gelatin | 2.42 gm$^{-2}$ |
| | Bis(vinylsulphonyl)-methane (hardener) | 0.06 gm$^{-2}$ |
| Support | Cellulose acetate | |

The coupler dispersion used contained 6% w/w gelatin, 8.8% coupler and coupler solvents in the ratio: coupler: tricresyl phosphate: 2- (2-butoxyethoxy )ethyl acetate 1:0.5:1.5.

The experimental photographic coatings prepared in this way are slit and chopped into 35 mm test strips. These are exposed through a 0–4.0 neutral density step wedge (0.2 ND step increments) and Daylight V, Wratten 9 filters then processed through the following standard C-41 process.

| Developer | 2.5 minutes |
|---|---|
| Bleach | 4 minutes |
| Wash | 2 minutes |
| Fix | 4 minutes |
| Wash | 2 minutes |

For each test strip, step-wedge densities are measured using a Macbeth TD/504/Hewlett Packard 85 automatic transmission densitometer. Measurements of minimum density (Dmin), maximum density (Dmax) and contrast (gamma) are calculated from D log E curves.

A comparison of the photographic results obtained from these tests is shown in Table 1.

TABLE 1

Photographic Performance of Compound 9 vs Control Couplers I, II and III

| Compound | D-min | D-max | Gamma | L-max |
|---|---|---|---|---|
| 9 | 0.39 | 2.42 | 3.77 | 555 nm |
| I | 0.13 | 2.32 | 2.29 | 555.5 nm |
| II | 0.15 | 2.77 | 4.01 | 546.5 nm |
| III | 0.14 | 2.62 | 2.08 | 553 nm |

The results show that compound 9 produces a dye of similarly desirable spatial absorption as compound III but has a much higher gamma (context). The dye produced for compound 9 has much lower blue absorption than those for compounds I and II.

What is claimed is:

1. A method for the production of a photographic element comprising an activated propene as a color coupler which method comprises reacting a compound of the formula (I)

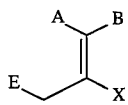

(I)

with nucleophile D to provide a compound of the formula (II)

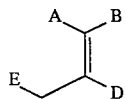

(II)

wherein A, B and E each individually represent hydrogen, a substituted or unsubstituted alkyl, acyl, carboxy or aryl group or an electron withdrawing group, and X is a group capable of displacement via a substitution reaction, and incorporating the same into a photographic element so as to be associated with a green-sensitive emulsion.

2. A method according to claim 1 wherein substituents A, B and E are alkyl or substituted alkyl and are selected from aralkyl, cycloalkyl, alkyl (carbonyl)oxy, alkoxycarbonyl, alkylaminocarbonyl, alkoxycarbonylamino, alkylsulphonylamino, alkylsulphonyl and an alkylthio group.

3. A method according to claim 1 wherein substituents A, B or E each individually represent a member selected from aryl (carbonyl)oxy, arylaminocarbonyl, acylamino, arylsulphonylamino, arylsulphonyl and arylthio.

4. A method according to claim 1 wherein substituents A, B or E each individually represent a member selected from an unsubstituted carboxy group or an electron withdrawing group selected from —CN, —NO$_2$, —SO$_2$R, —SO$_2$, —COH, —COR, —CONHR, CF$_3$, carbamoyl, ureido, sulphamoylamino, sulphamoyl, imido and a heterocycle, wherein R may be a substituted or unsubstituted alkyl or aryl group.

5. A method according to claim 1 wherein the compound of the formula (I) is a malonitrile dimer and wherein the nucleophile is anilino or a substituted anilino group.

6. A method according to claim 1 wherein the substituent D is selected from

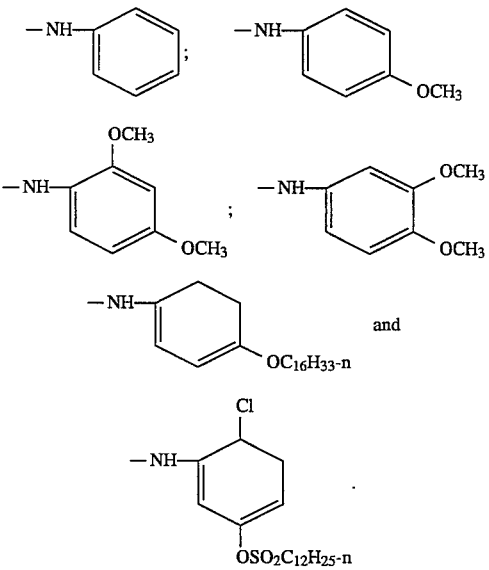

7. A method according to claim 1 wherein the nucleophile D forms a ballast substituent so as to render the resultant compound particularly suitable for use as a photographic coupler.

8. The method of claim 1 wherein X is selected from the group consisting of halogen, —NO$_2$, —NH$_2$, —SR, —SO$_2$R, —OSO$_2$R, and —OCOR wherein R is a substituted or unsubstituted alkyl or aryl group.

9. The method of claim 14 wherein E is an unsubstituted carboxy group or an electron withdrawing group selected from the group consisting of —CN, —NO$_2$, —SO$_2$R, —SO$_2$NH, —COH, —COR, —CONHR, —CF$_3$, carbamoyl, ureido, sulphamoylamino, sulphamoyl, imido, and a heterocycte wherein R is a substituted or unsubstituted alkyl or aryl group.

10. A method for the production of a photographic element comprising an activated propene as a color coupler which method comprises reacting a compound of the formula (I)

(I)

with nucleophile D to provide a compound of the formula (II)

(II)

wherein A, B and E each individually represent a member selected from an unsubstituted carboxy group or an electron withdrawing group selected from —CN, —NO$_2$, —SO$_2$R, —SO$_2$NH, —COH, —COR, —CONHR, —CF$_3$, carbamoyl, ureido, sulphamoylamino, sulphamoyl, imido, and a heterocycle, wherein R may be a substituted or unsubstituted alkyl or aryl group, and X is a group capable of displacement via a substitution reaction, and incorporating the same into a photographic element.

* * * * *